(12) United States Patent
Jiang et al.

(10) Patent No.: US 12,060,621 B2
(45) Date of Patent: Aug. 13, 2024

(54) SYSTEM FOR PREPARING XYLOSE LIQUID BY CONTINUOUSLY HYDROLYZING HEMICELLULOSE AND METHOD THEREOF

(71) Applicants: Zhejiang Huakang Pharmaceutical Co., Ltd., Zhejiang (CN); Jiaozuo Huakang Polyol Co., Ltd., Henan (CN)

(72) Inventors: Songtao Jiang, Zhejiang (CN); Chengjun Liao, Zhejiang (CN); Guowei Luo, Zhejiang (CN); Yuan Zhou, Zhejiang (CN); Shuncheng Fang, Zhejiang (CN); Yi Zheng, Zhejiang (CN); Xuesong Jiang, Zhejiang (CN); Xiaoyang Zheng, Zhejiang (CN)

(73) Assignees: ZHEJIANG HUAKANG PHARMACEUTICAL CO., LTD., Zhejiang (CN); JIAOZUO HUAKANG POLYOL CO., LTD., Henan (CN)

( * ) Notice: Subject to any disclaimer, the term of this patent is extended or adjusted under 35 U.S.C. 154(b) by 569 days.

(21) Appl. No.: 17/287,887

(22) PCT Filed: Nov. 26, 2019

(86) PCT No.: PCT/CN2019/121084
§ 371 (c)(1),
(2) Date: Apr. 22, 2021

(87) PCT Pub. No.: WO2020/114284
PCT Pub. Date: Jun. 11, 2020

(65) Prior Publication Data
US 2021/0348244 A1    Nov. 11, 2021

(30) Foreign Application Priority Data
Dec. 4, 2018 (CN) .................. 201811473078.X (51) Int. Cl.
*C13K 13/00* (2006.01)
*B01J 19/00* (2006.01)
*B01J 19/24* (2006.01)

(52) U.S. Cl.
CPC ......... *C13K 13/002* (2013.01); *B01J 19/0066* (2013.01); *B01J 19/0086* (2013.01);
(Continued)

(58) Field of Classification Search
CPC . C13K 13/002; B01J 19/0066; B01J 19/0086; B01J 19/249; B01J 2219/00051;
(Continued)

(56) References Cited

U.S. PATENT DOCUMENTS

| 5,705,369 A | 1/1998 | Torget et al. |
| 6,569,653 B1 * | 5/2003 | Alard .................. C12P 7/06 426/11 |

(Continued)

FOREIGN PATENT DOCUMENTS

| CN | 101457261 | 6/2009 |
| CN | 101818217 | 9/2010 |

(Continued)

OTHER PUBLICATIONS

English Translation of Bao Patent Publication CN 204685100U, published Oct. 7, 2015 (Year: 2015).*
(Continued)

*Primary Examiner* — Joseph W Drodge
(74) *Attorney, Agent, or Firm* — Fish & Richardson P.C.

(57) ABSTRACT

Related to is a system for preparing xylose liquid by continuously hydrolyzing hemicellulose, including a neutralizing unit, an acid-adjusting unit, a feeding unit, a liquefaction ejecting unit, a feed and discharge heat-exchanging unit and a discharge controlling unit. The neutralizing unit includes a raw material tank, a neutralizing
(Continued)

concentrated sulfuric acid pump and a neutralizing pipeline mixer, the acid-adjusting unit includes an acid-adjusting concentrated sulfuric acid pump, an acid-adjusting pipeline mixer and an acid-adjusting tank, the feeding unit includes a feed tank, the liquefaction ejecting unit includes a liquefaction ejector and a liquefaction maintainer, the feed and discharge heat-exchanging unit includes a plate-type teed and discharge heat exchanger and a first discharge temperature sensor, and the discharge controlling unit includes a discharge valve and a reflux valve. The obtained xylose liquid exchanges heat with the hemicellulose liquid in the plate-type feed and discharge heat exchanger to decrease a temperature of the xylose liquid, whereas a temperature of the hemicellulose liquid is increased. Further disclosed is a method using the system. The simultaneous feed and discharge heat exchanges greatly reduce energy consumption, and feed and exchange are continuously run, thereby improving the production efficiency and simplifying manual operations.

20 Claims, 1 Drawing Sheet

(52) U.S. Cl.
CPC .... *B01J 19/249* (2013.01); *B01J 2219/00051* (2013.01); *B01J 2219/00074* (2013.01); *B01J 2219/00164* (2013.01); *B01J 2219/00177* (2013.01); *B01J 2219/247* (2013.01)

(58) Field of Classification Search
CPC .... B01J 2219/00074; B01J 2219/00164; B01J 2219/00177; B01J 2219/247; B01J 4/008; B01J 19/0013; B01J 2219/0059; B01J 2219/00686; C12P 2201/00; C12P 19/02; B01F 35/2115; B01F 35/221; B01F 35/2215; B01F 35/7547; B01F 35/75471
USPC ..................................................... 127/1, 2
See application file for complete search history.

(56) References Cited

U.S. PATENT DOCUMENTS

| | | |
|---|---|---|
| 9,284,382 B2 | 3/2016 | Chen et al. |
| 2012/0052534 A1* | 3/2012 | Harlick ................ C12M 45/06 |
| | | 435/293.1 |
| 2015/0211026 A1* | 7/2015 | Bazzana .................. C12P 7/10 |
| | | 435/141 |
| 2016/0244788 A1* | 8/2016 | Retsina .................... D21C 3/00 |
| 2019/0093184 A1* | 3/2019 | Carlson .................. C12P 19/02 |

FOREIGN PATENT DOCUMENTS

| | | | |
|---|---|---|---|
| CN | 101863737 | | 10/2010 |
| CN | 101935718 | | 1/2011 |
| CN | 102021251 | | 4/2011 |
| CN | 102021252 | | 4/2011 |
| CN | 103409315 | | 11/2013 |
| CN | 103449699 | | 12/2013 |
| CN | 104437060 | | 3/2015 |
| CN | 104805222 | | 7/2015 |
| CN | 204685100 U | * | 10/2015 |
| CN | 106834554 | | 6/2017 |
| CN | 109355443 | | 2/2019 |
| CN | 209193996 | | 8/2019 |
| EP | 3299394 | | 3/2018 |

OTHER PUBLICATIONS

PCT Search Report in International Appln. No. PCT/CN2019/121084, dated Jun. 11, 2020, 6 pages (with English translation).
Extended European Search Report in European Appln No. 19892774.1, dated Oct. 18, 2021, 3 pages.
Harris et al., "Two-Stage, Dilute Sulfuric Acid Hydrolysis of Wood: An Investigation of Fundamentals," United States Department of Agriculture, Forest Service, General Technical Report FPL-45, Oct. 1985, 77 pages.
International Preliminary Report on Patentability in International Appln. No. PCT/CN2019/121084, dated Jun. 8, 2021, 11 pages.
Makashima et al., "Development of continuous flow type hydrothermal reactor for hemicellulose fraction recovery from corncob," Bioresource Technology, Jun. 2009, 100(11):2842-2848.
Um et al., "Acid Hydrolysis of Hemicellulose in Green Liquor Pre-Pulping Extract of Mixed Northern Hardwoods," Applied Biochemistry and Biotechnology, May 2009, 153(1-3):127-138.
Jin et al., "Kinetics of hemicellulose hydrolysis by dilute acid with cycle spray flow-through," CIESC Journal, Jan. 2011, 62(1):103-110 (with English abstract).
Yuan et al., "The Kinetics Studies on Hydrolysis of Hemicellulose," Frontiers in Chemistry, Nov. 2021, 9:781291, 12 pages.

* cited by examiner

SYSTEM FOR PREPARING XYLOSE LIQUID BY CONTINUOUSLY HYDROLYZING HEMICELLULOSE AND METHOD THEREOF

CROSS REFERENCE TO RELATED APPLICATIONS

This application is a national phase filing under 35 U.S.C. § 371 of International Application No. PCT/CN2019/121084, filed Nov. 26, 2019, which claims priority from Chinese Application No. 201811473078.X, filed Dec. 4, 2018. The entire contents of the prior applications are incorporated herein by reference in their entirety.

FIELD OF THE INVENTION

The present disclosure belongs to the technical field of xylose preparation through biomass acidolysis, and particularly relates to a system for preparing xylose liquid by continuously hydrolyzing hemicellulose and a method thereof.

BACKGROUND OF THE INVENTION

At present, a domestic xylose production method mainly obtains xylose liquid by performing dilute acid hydrolysis of corn cobs. The method generally adopts a kettle-type batch hydrolysis reaction, and the batch hydrolysis method has many shortcomings: 1. feed and discharge operations of reaction are complex; 2. non-environmental friendliness and large energy consumption: the in-kettle discharge energy cannot be well utilized after hydrolysis completion, resulting in large energy waste. Because corn cobs are main raw material for domestic xylose production, much residue is produced during hydrolysis which causes apparatus and pipelines to be blocked. At present, there is still no ideal continuous hydrolysis apparatus.

In a production process, viscose fibers with chemical pulp (plant cellulose such as wood pulp, cotton pulp, straw pulp and reed pulp) as raw material. To ensure the cellulose content during production, cellulose is treated (dipped and pressed) with alkaline liquid and hemicellulose is dissolved and separated. The alkaline liquid is filtered and recovered from the above hemicellulose alkaline liquid through nano-filtration and the remaining hemicellulose liquid is not well utilized, thereby causing wastes of resources.

SUMMARY OF THE INVENTION

To solve the technical problems, the present disclosure provides a system for preparing xylose liquid by continuously hydrolyzing hemicellulose and a method thereof. Due to a high automation degree, acidity may be continuously and automatically adjusted, feed and discharge may be continuously performed, and heat exchange may be continuously performed for the feed and discharge. By automatic programming control, continuous production can be achieved, and therefore, the present disclosure is suitable for industrialization.

The present disclosure is achieved by providing a system for preparing xylose liquid by continuously hydrolyzing hemicellulose, including a neutralizing unit, an acid-adjusting unit, a feeding unit, a liquefaction ejecting unit, a feed and discharge heat-exchanging unit and a discharge controlling unit. The neutralizing unit includes a raw material tank, a neutralizing concentrated sulfuric acid pump and a neutralizing pipeline mixer. The acid-adjusting unit includes an acid-adjusting concentrated sulfuric acid pump, an acid-adjusting pipeline mixer and an acid-adjusting tank. The feeding unit includes a feed tank, the liquefaction ejecting unit includes a liquefaction ejector and a liquefaction maintainer, the feed and discharge heat-exchanging unit includes a plate-type feed and discharge heat exchanger and a first discharge temperature sensor, and the discharge controlling unit includes a discharge valve and a reflux valve. The raw material tank is used to store hemicellulose alkaline liquid, the neutralizing pipeline mixer is used to perform neutralization reaction for the hemicellulose alkaline liquid and the concentrated sulfuric acid from the neutralizing concentrated sulfuric acid pump to obtain a hemicellulose liquid raw material, the acid-adjusting pipeline mixer is used to mix the hemicellulose liquid raw material with the concentrated sulfuric acid from the acid-adjusting concentrated sulfuric acid pump to obtain a hemicellulose liquid, the acid-adjusting tank collects the mixed hemicellulose liquid, the feed tank receives the hemicellulose liquid overflowing from the acid-adjusting tank, the plate-type feed and discharge heat exchanger is used to exchange heat between the feed of the acid-adjusted hemicellulose liquid and the xylose liquid obtained by hydrolysis, the liquefaction ejector is used to fully mix the heat-exchanged hemicellulose liquid with external high-pressure vapour and eject them together into the liquefaction maintainer, which is used to perform hydrolysis reaction for the hemicellulose liquid and water vapour at a high temperature to obtain the xylose liquid, the first discharge temperature sensor is used to sense the temperature of the xylose liquid obtained by hydrolysis, and the first discharge temperature sensor is interlocked with the discharge valve and the reflux valve to control a flow direction of the xylose liquid obtained by hydrolysis. When the first discharge temperature sensor senses that the temperature of the xylose liquid is not lower than a set value, the discharge valve of the discharge controlling unit is opened, the reflux valve of the discharge controlling unit is closed, and the xylose liquid is discharged normally; otherwise, the reflux valve is opened, the discharge valve is closed, and the xylose liquid flows back into the feed tank for recirculation.

Further, the neutralizing unit includes a raw material switching valve, a material pump, a neutralizing sulfuric acid switching valve, a neutralizing sulfuric acid flow controller and a neutralization pH controller. The raw material switching valve is used to control the hemicellulose alkaline liquid in the raw material tank to flow out or stop flowing, the neutralizing sulfuric acid switching valve is used to control on and off of an output pipeline of the neutralizing concentrated sulfuric acid pump, the neutralizing sulfuric acid flow controller is used to control a flow rate of the concentrated sulfuric acid in the output pipeline of the neutralizing concentrated sulfuric acid pump, the material pump is used to transport the neutralized hemicellulose liquid raw material to the acid-adjusting unit, and the neutralization pH controller is used to control the pH value of the mixed hemicellulose liquid raw material.

Further, the acid-adjusting unit includes a material flow controller and an acid-adjusting sulfuric acid flow controller. The material flow controller is used to control a flow rate of the flowing hemicellulose liquid raw material, the acid-adjusting sulfuric acid flow controller is used to control a flow rate of the concentrated sulfuric acid in a transport pipeline of the acid-adjusting concentrated sulfuric acid pump, and the material flow controller is linked with the acid-adjusting sulfuric acid flow controller to adjust a pumping amount of the acid-adjusting concentrated sulfuric acid pump according to the flow rate of the hemicellulose liquid raw material, so that the acidity of the hemicellulose liquid raw material satisfies a set value.

Further, the feeding unit includes a feed pump and a feed valve switch. The feed pump is used to transport the hemicellulose liquid in the feed tank to the feed and discharge heat-exchanging unit, and the feed valve switch is used to control on and off of a transport pipeline of the feed pump. The liquefaction ejecting unit further includes a liquefaction temperature controller and a temperature regulating valve. The liquefaction temperature controller is used to control a temperature of the hemicellulose liquid entering the liquefaction maintainer, the liquefaction temperature controller is linked with the temperature regulating valve, and the temperature regulating valve is used to control an opening degree of the liquefaction ejector and maintain a stable temperature of the liquefaction maintainer so as to facilitate hydrolysis of the hemicellulose liquid.

Further, the feed and discharge heat-exchanging unit includes a feed adjusting valve, and the feed adjusting valve controls the flow rate of the hemicellulose liquid in the pipeline.

Further, the discharge controlling unit includes a plate-type discharge heat exchanger, a second discharge temperature controller and a discharge pressure adjusting valve. The plate-type discharge heat exchanger is used to exchange heat for the flowing xylose liquid with cooling water so as to reduce the temperature of the xylose liquid, the second discharge temperature controller is used to control the temperature of the xylose liquid before discharge, and the discharge pressure adjusting valve is used to control a pressure of the xylose liquid before discharge.

The present disclosure is achieved by providing a method of preparing xylose liquid by continuously hydrolyzing hemicellulose. The method using the system for preparing xylose liquid by continuously hydrolyzing hemicellulose as described above includes the following steps 1-6.

At step 1, in a neutralizing procedure, when hemicellulose alkaline liquid stored in the raw material tank reaches 25%-35%, the raw material switching valve is opened to allow the hemicellulose alkaline liquid to enter the neutralizing pipeline mixer through the raw material switching valve, concentrated sulfuric acid pumped by the neutralizing concentrated sulfuric acid pump also enters the neutralizing pipeline mixer after passing through the neutralizing sulfuric acid flow controller to be mixed with the hemicellulose alkaline liquid in the neutralizing pipeline mixer for neutralization reaction, the neutralizing concentrated sulfuric acid pump is interlocked with the neutralizing sulfuric acid controller, and the neutralizing sulfuric acid controller is interlocked with the neutralization pH controller to control an amount of the concentrated sulfuric acid pumped by the neutralizing concentrated sulfuric acid pump and stabilize the pH value of the neutralized hemicellulose liquid raw material at a set value of 6.5-7.0.

At step 2, in an acid-adjusting procedure, the neutralized hemicellulose liquid raw material is transported to the acid-adjusting pipeline mixer of the acid-adjusting unit through the material pump, concentrated sulfuric acid pumped by the acid-adjusting concentrated sulfuric acid pump also enters the acid-adjusting pipeline mixer after passing through the acid-adjusting sulfuric acid controller to be mixed with the hemicellulose liquid raw material in the acid-adjusting pipeline mixer, the mixed hemicellulose liquid enters the acid adjusting tank for temporary storage, and the acid-adjusting sulfuric acid controller is linked with the material flow controller to adjust a pumping amount of the acid-adjusting concentrated sulfuric acid pump according to the flow rate of the hemicellulose liquid raw material to enable the acidity of the hemicellulose liquid raw material to satisfy a set requirement of 1%-4%.

At step 3, in a feeding procedure, the acid-adjusted hemicellulose liquid enters the feed tank of the feeding unit from the acid-adjusting tank through overflow; when a liquid level of the feed tank reaches 25%-35%, the feed valve switch and the feed pump are opened to allow the hemicellulose liquid to enter a subsequent procedure.

At step 4, in a liquefaction ejecting procedure, after flowing through the plate-type feed and discharge heat exchanger, the hemicellulose liquid enters the liquefaction ejector to be mixed with external high-pressure vapour in the liquefaction ejector and ejected into the liquefaction maintainer together with the vapour, and the xylose liquid is obtained after hydrolysis reaction occurs between the hemicellulose liquid and water vapour in the liquefaction maintainer; the liquefaction temperature controller is linked with the temperature regulating valve, and the temperature regulating valve controls an opening degree of the liquefaction ejector and maintains a stable temperature of the liquefaction maintainer to facilitate the hydrolysis of the hemicellulose liquid; hydrolysis time of the hemicellulose liquid in the liquefaction maintainer is maintained in 2.0 h to 3.0 h.

At step 5, in a feed and discharge heat-exchanging procedure, the temperature of the obtained xylose liquid has a decreased temperature after passing through the plate-type feed and discharge heat exchanger to exchange heat with the hemicellulose liquid from the feed pump, whereas the temperature of the hemicellulose liquid is increased due to residual heat of the hemicellulose liquid, and the first discharge temperature sensor is interlocked with the discharge valve and the reflux valve of the discharge controlling unit; when the first discharge temperature sensor senses that the temperature of the xylose liquid is not lower than a set value, the discharge valve of the discharge controlling unit is opened, the reflux valve of the discharge controlling unit is closed, and the xylose liquid is discharged normally; otherwise, the reflux valve is opened, the discharge valve is closed, and the xylose liquid flows back into the feed tank for recirculation.

At step 6, in a discharge controlling procedure, the heat-exchanged xylose liquid enters the plate-type discharge heat exchanger to exchange heat with cooling water flowing through the plate-type discharge heat exchanger and thus has a further reduced temperature. After flowing through the discharge pressure adjusting valve and the second discharge temperature controller, the xylose liquid satisfying set pressure and temperature conditions is discharged from the discharge valve.

Further, at step 4, a sensing temperature of the liquefaction temperature controller is set between 128° C. and 130° C.

Further, at step 5, a sensing temperature of the first discharge temperature sensor is set between 115° C. and 120° C. When the temperature of the hydrolyzed xylose liquid is lower than 115° C., the reflux valve is opened, the discharge valve is closed, and the xylose liquid flows back into the feed tank for recirculation.

Further, at step 6, a discharge temperature of the xylose liquid is stabilized at 60° C. to 80° C., with a pressure range between 0.20 MPa and 0.30 MPa.

Compared with the prior art, the system for preparing xylose liquid by continuously hydrolyzing hemicellulose and the method thereof according to the present disclosure are characterized in that the acidity of the hemicellulose liquid material is controlled through an online pH monitor and flow interlocking, the plate-type feed and discharge heat exchanger performs heat exchange of feed and discharge by fully using the residual heat of hydrolysate, the liquefaction temperature sensor controls the opening degree of the liquefaction ejector to control the hydrolysis temperature, the pressure range of the hydrolysis process is ensured through discharge pressure interlocking, and the discharge of the xylose liquid is water-cooled to allow its discharge temperature to satisfy the next procedure. Further, the continuous and stable hydrolysis of the hemicellulose can be automatically controlled only by setting parameters well according to conditions of the hemicellulose liquid material. Meanwhile, the apparatus of the system is high in energy utilization rate, and convenient to operate, and thus can realize efficient and controllable continuous production.

DETAILED DESCRIPTION OF THE EMBODIMENTS

To understand the technical problems to be solved, technical solutions and beneficial effects of the present disclosure more clearly, the present disclosure will be further described in detail below in combination with accompanying drawings and embodiments. It is to be understood that the specific embodiments described herein are only used to explain the present disclosure rather than limit the present disclosure.

Figure 1:
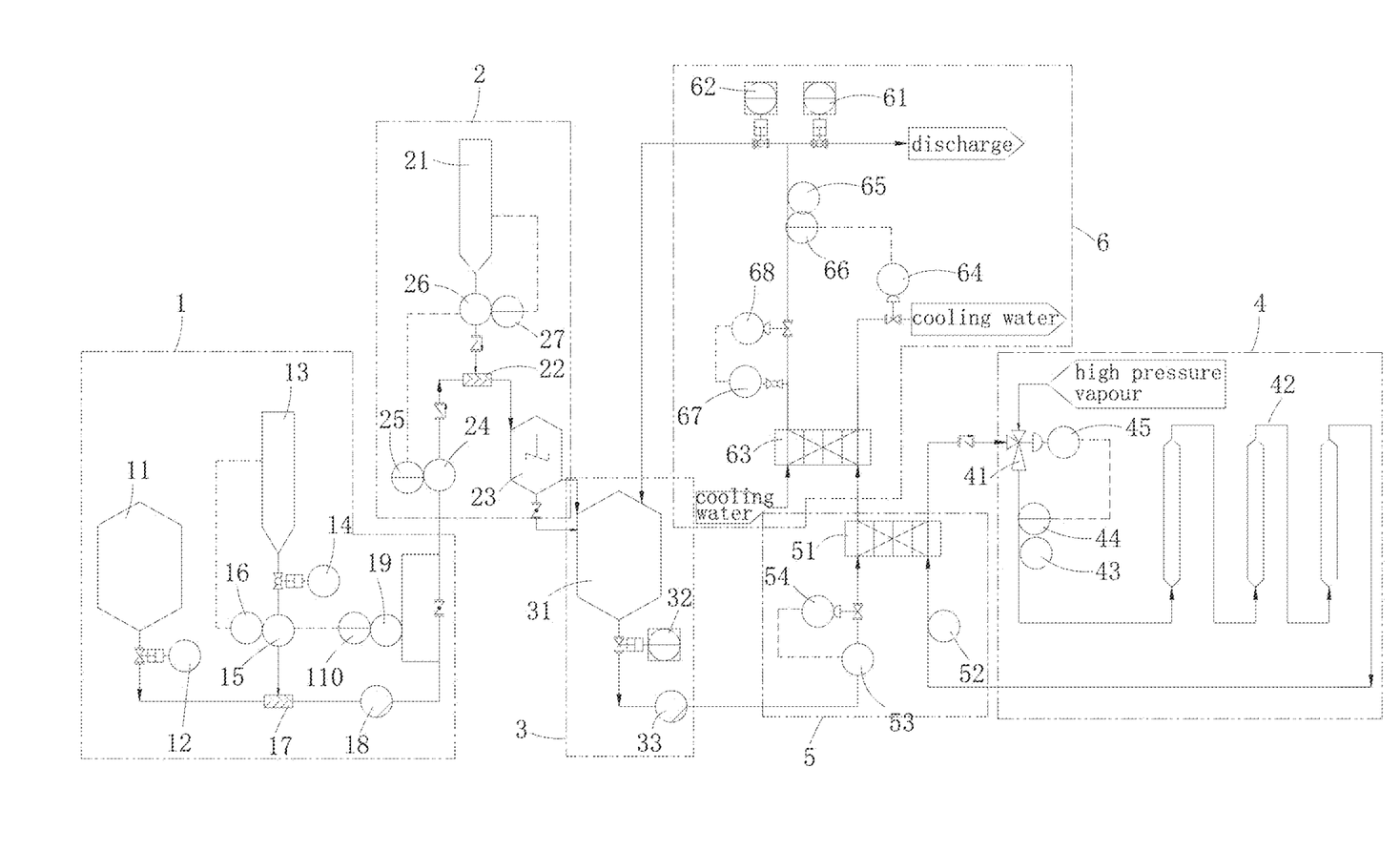
FIG. 1 is a principle diagram illustrating a system for preparing xylose liquid by continuously hydrolyzing hemicellulose according to a preferred embodiment of the present disclosure.

FIG. 1 illustrates a preferred embodiment of a system for preparing xylose liquid by continuously hydrolyzing hemicellulose according to the present disclosure. The system includes a neutralizing unit 1, an acid-adjusting unit 2, a feeding unit 3, a liquefaction ejecting unit 4, a feed and discharge heat-exchanging unit 5 and a discharge controlling unit 6.

The neutralizing unit 1 includes a raw material tank 11, a raw material switching valve 12, a neutralizing concentrated sulfuric acid pump 13, a neutralizing sulfuric acid switching valve 14, a neutralizing sulfuric acid flow gauge 15, a neutralizing sulfuric acid flow controller 16, a neutralizing pipeline mixer 17, a material pump 18, a neutralization pH sensor 19 and a neutralization pH controller 11. The raw material tank 11 is used to store hemicellulose alkaline liquid. The neutralizing concentrated sulfuric acid pump 13 is a variable frequency pump. The neutralizing pipeline mixer 17 is used to perform neutralization reaction for the hemicellulose alkaline liquid and concentrated sulfuric acid from the neutralizing concentrated sulfuric acid pump 13 to obtain hemicellulose liquid raw material. The raw material switching valve 12 is used to control the hemicellulose alkaline liquid in the raw material tank 11 to flow out or stop flowing. The neutralizing sulfuric acid switching valve 14 is used to control on and off of an output pipeline of the neutralizing concentrated sulfuric acid pump 13. The neutralizing sulfuric acid flow gauge 15 and the neutralizing sulfuric acid flow controller 16 are used to sense a flow rate of the concentrated sulfuric acid in the output pipeline of the neutralizing concentrated sulfuric acid pump 13. The material pump 18 is used to transport the neutralized hemicellulose liquid raw material to the acid-adjusting unit 2. The neutralization sensor 19 and the neutralization pH controller 110 are used to sense and control the pH value of the mixed hemicellulose liquid raw material.

The acid-adjusting unit 2 includes an acid-adjusting concentrated sulfuric acid pump 21, an acid-adjusting pipeline mixer 22, an acid-adjusting tank 23, a material flow gauge 24, a material flow controller 25, an acid-adjusting sulfuric acid flow gauge 26 and an acid-adjusting sulfuric acid flow controller 27. The acid-adjusting concentrated sulfuric acid, pump 21 is a variable frequency pump. The acid-adjusting pipeline mixer 22 is used to mix the hemicellulose liquid raw material with the concentrated sulfuric acid from the acid-adjusting concentrated sulfuric acid pump 21 to obtain hemicellulose liquid. The acid-adjusting tank 23 collects the mixed hemicellulose liquid. The material flow gauge 24 and the material flow controller 25 are used to sense and control a flow rate of the flowing cellulose liquid raw material. The acid-adjusting sulfuric acid flow gauge 26 and the acid-adjusting sulfuric acid flow controller 27 are used to sense and control the flow rate of the concentrated sulfuric acid in the transport pipeline of the acid-adjusting concentrated sulfuric acid pump 21. The material flow gauge 24 and the material flow controller 25 are linked with the acid-adjusting sulfuric acid flow gauge 26 and the acid-adjusting sulfuric acid flow controller 27 to adjust a pumping amount of the acid-adjusting concentrated sulfuric acid pump 21 according to the flow rate of the hemicellulose liquid raw material, so that the acidity of the hemicellulose liquid raw material satisfies a set value.

The feeding unit 3 includes a feed tank 31, a feed valve switch 32 and a feed pump 33. The feed tank 31 receives the hemicellulose liquid overflowing from the acid-adjusting tank 23. The feed pump 33 is used to transport the hemicellulose liquid in the feed tank 31 to the feed and discharge heat-exchanging unit 5. The feed valve switch 32 is used to control on and off of the transport pipeline of the feed pump 33.

The liquefaction ejecting unit 4 includes a liquefaction ejector 41, a liquefaction maintainer 42, a liquefaction temperature sensor 43, a liquefaction temperature controller 44 and a temperature regulating valve 45. The liquefaction ejector 41 is used to fully mix the heat-exchanged hemicellulose liquid with external high-pressure vapour and eject them together into the liquefaction maintainer 42. The liquefaction temperature controller 44 is used to control a temperature of the hemicellulose liquid entering the liquefaction maintainer 42. After flowing through the plate-type feed and discharge heat exchanger 51, the hemicellulose liquid is mixed with the external high-pressure vapour in the liquefaction ejector 41 and ejected into the liquefaction maintainer 42 together with the vapour, and the xylose liquid is obtained after hydrolysis reaction occurs between the hemicellulose liquid and the water vapour in the liquefaction maintainer 42. The liquefaction temperature sensor 43 and the liquefaction temperature controller 44 are linked with the temperature regulating valve 45, and the temperature regulating valve 45 is used to control an opening degree of the liquefaction ejector 41 and maintain a stable temperature of the liquefaction maintainer 42 so as to facilitate the hydrolysis of the hemicellulose liquid.

The feed and discharge heat-exchanging unit 5 includes a plate-type feed and discharge heat exchanger 51, a first discharge temperature sensor 52, a feed flow gauge 53 and a feed adjusting valve 54. The plate-type feed and discharge heat exchanger 51 is used to exchange heat between feed of the acid-adjusted hemicellulose liquid and the xylose liquid obtained by hydrolysis. The xylose liquid obtained from the liquefaction ejecting unit 4 exchanges heat with the hemicellulose liquid from the feed tank 31 in the plate-type feed and discharge heat exchanger 51 so that the temperature of the xylose liquid is decreased, whereas the temperature of the hemicellulose liquid is increased. At the same time, the heat exchange of feed and discharge can greatly reduce energy consumption. The first discharge temperature sensor 52 is used to sense the temperature of the xylose liquid obtained by hydrolysis. The feed flow gauge 53 is used to sense the flow rate of the flowing hemicellulose liquid from the feed pump 33. The feed flow gauge 53 and the feed adjusting valve 54 are linked with each other to control the flow rate of the hemicellulose liquid in the pipeline.

The discharge temperature of the xylose liquid is a criterion for determining whether the hydrolysis of the xylose liquid is sufficient. When the discharge temperature does not reach a set target value, it is considered that the hydrolysis reaction of the hemicellulose liquid is insufficient, and the xylose liquid must flow back for recirculation. The hydrolysis reaction of the hemicellulose liquid is considered as sufficient only when the discharge temperature reaches the set target value. Generally, the apparatus of the system of the present disclosure requires a backflow process only when the apparatus is just started operating, and discharges in a direct flow when the system apparatus works normally.

The discharge controlling unit 6 includes a discharge valve 61, a reflux valve 62, a plate-type discharge heat exchanger 63, a cooling water temperature regulating valve 64, a second discharge temperature sensor 65, a second discharge temperature controller 66, a discharge pressure sensor 67 and a discharge pressure adjusting valve 68.

The first discharge temperature sensor 52 is interlocked with the discharge valve 61 and the reflux valve 62 to control a flow direction of the xylose liquid obtained by hydrolysis. When the first discharge temperature sensor 52 senses that the temperature of the xylose liquid is not lower than the set value, the discharge valve 61 is opened, the reflux valve 62 is closed, and the xylose liquid is discharged normally; otherwise, the reflux valve 62 is opened, the discharge valve 61 is closed, and the xylose liquid flows back into the feed tank 31 for recirculation. The discharge temperature of the xylose liquid is controlled to ensure the sufficient hydrolysis reaction of the hemicellulose liquid, thereby improving the conversion efficiency of the hemicellulose liquid.

The plate-type discharge heat exchanger 63 is used to perform heat exchange for the flowing xylose liquid with cooling water so as to decrease the temperature of the xylose liquid. The cooling water temperature regulating valve 64 is used to adjust a temperature of the cooling water. Water cooling is performed for the discharge of the xylose liquid to enable the discharge temperature of the xylose liquid to satisfy the next procedure. The second discharge temperature sensor 65 and the second discharge temperature controller 66 are used to sense and control the temperature of the xylose liquid before discharge. The discharge pressure sensor 67 and the discharge pressure adjusting valve 68 are used to sense and control the pressure of the xylose liquid before discharge.

The present disclosure further provides a method of preparing xylose liquid by continuously hydrolyzing hemicellulose. The method employs a system for preparing xylose liquid by continuously hydrolyzing hemicellulose as described above and includes the following steps.

At step 1, in a neutralizing procedure, when hemicellulose alkaline liquid stored in the raw material tank 11 reaches 25%-35%, the raw material switching valve 12 is opened to allow the hemicellulose alkaline liquid to enter the neutralizing pipeline mixer 17 through the raw material switching valve 12 as shown by arrows in the FIG. After passing through the neutralizing sulfuric acid switching valve 14, the neutralizing sulfuric acid flow gauge 15 and the neutralizing sulfuric acid flow controller 16, concentrated sulfuric acid pumped by the neutralizing concentrated sulfuric acid pump 13 also enters the neutralizing pipeline mixer 17 to perform neutralization reaction with the hemicellulose alkaline liquid in the neutralizing pipeline mixer 17. The neutralized hemicellulose liquid is transported to the acid-adjusting unit 2 through the material pump 18. The material pump 18 is provided with a variable frequency function capable of automatically adjusting a flow rate according to a set value of the neutralizing sulfuric acid flow gauge 15. The neutralization pH sensor 19 disposed in a transport pipeline senses a pH value of the hemicellulose liquid, and controls the neutralizing sulfuric acid flow gauge 15 and the neutralizing sulfuric acid flow controller 16 through the neutralization pH controller 110 to adjust an Output amount of the concentrated sulfuric acid of the neutralizing concentrated sulfuric acid pump 13 so that a pH value of the neutralized hemicellulose liquid raw material is stabilized at a set value of 6.5-7.0.

At step 2, in an acid-adjusting procedure, the hemicellulose liquid raw material enters the acid-adjusting pipeline mixer 22 as shown by arrows in the FIG. After flowing through the acid-adjusting sulfuric acid flow gauge 26 and the acid-adjusting sulfuric acid flow controller 27, the concentrated sulfuric acid pumped by the acid-adjusting concentrated sulfuric acid pump 21 also enters the acid-adjusting pipeline mixer 22 to be mixed with the hemicellulose liquid raw material in the acid-adjusting pipeline mixer 22. The mixed hemicellulose liquid enters the acid-adjusting tank 23 for temporary storage. The material flow gauge 24 and the material flow controller 25 disposed in the transport pipeline of the hemicellulose liquid raw material are linked with the acid-adjusting sulfuric acid flow gauge 26 and the acid-adjusting sulfuric acid flow controller 27 to adjust a pumping amount of the acid-adjusting concentrated sulfuric acid pump 21 according to the flow rate of the hemicellulose liquid raw material, so that acidity of the hemicellulose liquid raw material satisfies a set requirement of 1%-4%, and the hemicellulose liquid in the acid-adjusting tank 23 enters the feeding unit 3 through the valve.

At step 3, in a feeding procedure, the acid-adjusted hemicellulose liquid enters the feed tank 31 of the feeding unit 3 from the acid-adjusting tank 23 through overflow as shown by arrows in the FIG. When a liquid level of the teed tank 31 reaches 25%-35%, the feed valve switch 32 is turned on and the feed pump 33 are started, so that the hemicellulose enters the feed and discharge heat-exchanging unit 5.

At step 4, in a liquefaction ejecting procedure, after flowing through the plate-type feed and discharge heat exchanger 51, the hemicellulose liquid enters the liquefaction ejector 41 to be mixed with external high-pressure vapour in the liquefaction ejector 41 and ejected into the liquefaction maintainer 42 together with the vapour as shown by arrows in the FIG. The xylose liquid is obtained after hydrolysis reaction occurs to the hemicellulose liquid and water vapour in the liquefaction maintainer 42. The liquefaction temperature sensor 43 and the liquefaction temperature controller 44 are linked with the temperature regulating valve 45, and the temperature regulating valve 45 controls an opening degree of the liquefaction ejector 41 to maintain a stable temperature of the liquefaction maintainer 42 so as to facilitate hydrolysis of the hemicellulose liquid;

a hydrolytic time of the hemicellulose liquid in the liquefaction maintainer 42 is maintained in 2.0 h to 3.0 h. A sensing temperature of the liquefaction temperature controller 44 is set between 128° C. and 130° C.

At step 5, in a feed and discharge heat-exchanging procedure, after passing through the feed adjusting valve 55 linked controlled by the feed flow controller 54 and the feed flow gauge 53, the hemicellulose liquid from the feed pump 32 enters the plate-type feed and discharge heat exchanger 51 to exchange heat with the high-temperature xylose liquid discharged from the liquefaction ejecting unit 4, and then enters the liquefaction ejector 41 of the liquefaction ejecting unit 4 as shown by arrow in the FIG. The first discharge temperature sensor 52 is interlocked with the discharge valve 61 and the reflux valve 62 of the discharge controlling unit 6. When the first discharge temperature sensor 52 senses that the temperature of the xylose liquid is not lower than the set value, the discharge valve 61 of the discharge controlling unit 6 is opened, the reflux valve 62 of the discharge controlling unit 6 is closed, and the xylose liquid is discharged normally; otherwise, the reflux valve 62 is opened, the discharge valve 61 is closed, and the xylose liquid flows back into the feed tank 31 for recirculation. A sensing temperature of the first discharge temperature sensor 52 is set between 115° C. and 120° C. When the temperature of the hydrolyzed xylose liquid is lower than 115° C., the reflux valve is opened, the discharge valve is closed, and the xylose liquid flows back into the feed tank for recirculation.

At step 6, in a discharge controlling procedure, the heat-exchanged xylose liquid enters the plate-type discharge heat exchanger 63 to exchange heat with cooling water flowing through the plate-type discharge heat exchanger 63, and thus has a further reduced temperature as shown by arrows in the drawing. After flowing through the discharge pressure sensor 67, the discharge pressure adjusting valve 68, the second discharge temperature sensor 65 and the second discharge temperature controller 66, the xylose liquid satisfying the set pressure and temperature conditions is discharged from the discharge valve as shown by arrows in the FIG. The second discharge temperature controller 66 is linked with the cooling water temperature regulating valve 64 to control a cooling temperature of the xylose liquid. A discharge temperature of the xylose liquid is stabilized at 60° C. to 80° C., with a pressure range being 0.20 MPa to 0.30 MPa.

The continuous feed and discharge control is performed for the feed of the hemicellulose liquid and the discharge of the xylose liquid by using the system for preparing xylose liquid by continuously hydrolyzing hemicellulose according to the present disclosure to improve a production efficiency of hydrolysis of the hemicellulose liquid, with high automation degree and simplified worker operations. The apparatus of the method of the present disclosure features continuous hydrolysis. Compared with the existing kettle-type batch hydrolysis, the method of the present disclosure has one advantage of saying operation time of feed and discharge and improving the hydrolysis efficiency (production capacity).

The system for preparing xylose liquid by continuously hydrolyzing hemicellulose liquid and the method thereof according to the present disclosure will be further described below in combination with specific embodiments.

Embodiment 1

Preparing xylose liquid by continuously hydrolyzing hemicellulose alkaline liquid (alkali concentration 1.5%, hemicellulose concentration 8% and a flow rate 6 m³/h) is taken as an example.

At step 1, in a neutralizing procedure, a neutralization endpoint of the pH sensor 19 was set to pH7, and the pH controller 110 interlockedly controlled a flow rate of concentrated sulfuric acid to 58 L/h, so that a frequency of neutralizing concentrated sulfuric acid pump 13 was interlockedly flow-controlled to 36 HZ. After passing through the neutralizing unit, the hemicellulose alkaline liquid was transported to the acid-adjusting unit through the material pump 18.

At step 2, in an acid-adjusting procedure, a flow rate of the material flow gauge 24 of the hemicellulose liquid raw material was 6 m³/h, and a flow rate of the acid-adjusting sulfuric acid flow gauge 26 was interlockedly controlled to 66 L/H to control a frequency of the acid-adjusting concentrated sulfuric acid pump 21 to 30 HZ.

At step 3, in a feed and discharge heat-exchanging procedure, a discharge sensing temperature of the first discharge temperature sensor 52 was 118° C., a flow rate of the feed flow gauge 53 was 6 m³/h, and the feed flow controller 54 interlockedly controlled an opening degree of the feed adjusting valve 55 to 60%.

At step 4, in a liquefaction ejecting procedure, a temperature of the liquefaction temperature sensor 43 was set to 128° C., and the liquefaction temperature controller 44 interlockedly temperature-controlled an opening degree of the liquefaction ejector 41 to 70% to ensure that the hemicellulose liquid at a stable temperature of 128° C. was liquefaction-ejected into the liquefaction maintainer 42 for hydrolysis. A cylinder of the liquefaction maintainer 42 was designed to have a volume capacity of 12 m³ to maintain a time from feed to discharge to 2 h.

At step 5, in a discharge controlling procedure, an opening degree of the discharge pressure adjusting valve 68 was 40%, and a pressure of the discharge pressure sensor was interlockedly controlled to 0.25 MPa; at the same time, the second discharge temperature sensor 65 and the second discharge temperature controller 66 interlockedly controlled, by temperature sensing, an opening degree of the cooling water temperature regulating valve 64 to 60%, and stably controlled a discharge endpoint temperature of the xylose liquid to 60° C. When a temperature of the first discharge temperature sensor 52 reached 115° C., the discharge valve 61 was opened; when the temperature of the first discharge temperature sensor 52 was lower than 115° C., the reflux valve 62 was opened.

The foregoing disclosure is merely illustrative of preferred embodiments of the present disclosure but not intended to limit the present disclosure, and any modifications, equivalent substitutions and improvements made within the spirit and principles of the present disclosure shall be encompassed in the scope of protection of the present disclosure.

The invention claimed is:

1. A system for preparing xylose liquid by continuously hydrolyzing hemicellulose, comprising a neutralizing unit, an acid-adjusting unit, a feeding unit, a liquefaction ejecting unit, a feed and discharge heat-exchanging unit and a discharge controlling unit, wherein:
   the neutralizing unit comprises a raw material tank, a neutralizing concentrated sulfuric acid pump and a neutralizing pipeline mixer,
   the acid-adjusting unit comprises an acid-adjusting concentrated sulfuric acid pump, an acid-adjusting pipeline mixer and an acid-adjusting tank,
   the feeding unit comprises a feed tank,
   the liquefaction ejecting unit comprises a liquefaction ejector and a liquefaction maintainer, the feed and discharge heat-exchanging unit comprises a plate-type feed and discharge heat exchanger and a first discharge temperature sensor, and
the discharge controlling unit comprises a discharge valve and a reflux valve, wherein:
the raw material tank is configured to store a hemicellulose alkaline liquid,
the neutralizing pipeline mixer is configured to perform a neutralization reaction of the hemicellulose alkaline liquid with sulfuric acid from the neutralizing concentrated sulfuric acid pump to obtain a hemicellulose liquid raw material,
the acid-adjusting pipeline mixer is configured to mix the hemicellulose liquid raw material with sulfuric acid from the acid-adjusting concentrated sulfuric acid pump to obtain an acid-adjusted hemicellulose liquid,
the acid-adjusting tank is configured to collect the acid-adjusted hemicellulose liquid,
the feed tank is configured to receive hemicellulose liquid overflowing from the acid-adjusting tank,
the plate-type feed and discharge heat exchanger is configured to exchange heat between feed of the acid-adjusted hemicellulose liquid from the feed tank and a xylose liquid obtained by hydrolysis,
the liquefaction ejector is configured to mix the heat-exchanged hemicellulose liquid with an external high-pressure vapor and eject the heat-exchanged hemicellulose liquid and the high-pressure vapor together into the liquefaction maintainer,
the liquefaction maintainer is configured to perform a hydrolysis reaction for the hemicellulose liquid and high-pressure vapor to obtain the xylose liquid,
the first discharge temperature sensor is configured to sense a temperature of the xylose liquid obtained by the hydrolysis reaction, and
the first discharge temperature sensor is interlocked with the discharge valve and the reflux valve to control a flow direction of the xylose liquid obtained by hydrolysis.

2. The system according to claim 1, wherein
the neutralizing unit further comprises a raw material switching valve, a material pump, a neutralizing sulfuric acid switching valve, a neutralizing sulfuric acid flow controller and a neutralization pH controller,
the raw material switching valve is configured to control the hemicellulose alkaline liquid in the raw material tank to flow or stop flowing,
the neutralizing sulfuric acid switching valve is configured to control flow on and off in an output pipeline of the neutralizing concentrated sulfuric acid pump,
the neutralizing sulfuric acid flow controller is configured to control a flow rate of the sulfuric acid in the output pipeline of the neutralizing concentrated sulfuric acid pump,
the material pump is configured to transport the neutralized hemicellulose liquid raw material to the acid-adjusting unit, and
the neutralization pH controller is configured to control a pH value of the hemicellulose liquid raw material.

3. The system according to claim 2, wherein
the acid-adjusting unit further comprises a material flow controller and an acid-adjusting sulfuric acid flow controller,
the material flow controller is configured to control a flow rate of the flowing hemicellulose liquid raw material,
the acid-adjusting sulfuric acid flow controller is configured to control a flow rate of the sulfuric acid,
the material flow controller is linked with the acid-adjusting sulfuric acid flow controller to adjust a pumping amount of the acid-adjusting concentrated sulfuric acid pump according to the flow rate of the hemicellulose liquid raw material so that the acidity of the hemicellulose liquid raw material satisfies a set value.

4. The system according to claim 3, wherein
the feeding unit further comprises a feed pump and a feed valve switch, wherein the feed pump is configured to transport the hemicellulose liquid in the feed tank to the feed and discharge heat-exchanging unit, and the feed valve switch is configured to control a flow of the hemicellulose liquid in a transport pipeline of the feed pump; and
the liquefaction ejecting unit further comprises a liquefaction temperature controller and a temperature regulating valve, wherein the liquefaction temperature controller is configured to control a temperature of the hemicellulose liquid entering the liquefaction maintainer, the liquefaction temperature controller is linked with the temperature regulating valve, and the temperature regulating valve is configured to control an opening degree of the liquefaction ejector to maintain a stable temperature of the liquefaction maintainer so as to facilitate hydrolysis of the hemicellulose liquid.

5. The system according to claim 4, wherein the feed and discharge heat-exchanging unit further comprises a feed adjusting valve, and the feed adjusting valve is configured to control a flow rate of the hemicellulose liquid in the pipeline.

6. The system according to claim 5, wherein the discharge controlling unit further comprises a plate-type discharge heat exchanger, a second discharge temperature controller and a discharge pressure adjusting valve, the plate-type discharge heat exchanger is configured to exchange heat for the flowing xylose liquid with cooling water so as to decrease the temperature of the xylose liquid, the second discharge temperature controller is configured to control the temperature of the xylose liquid before discharge, and the discharge pressure adjusting valve is configured to control a pressure of the xylose liquid before discharge.

7. A method of preparing xylose liquid by continuously hydrolyzing hemicellulose using the system according to claim 6, comprising the following steps:
at step 1, in a neutralizing procedure, when hemicellulose alkaline liquid stored in the raw material tank reaches 25%-35%, opening the raw material switching valve to allow the hemicellulose alkaline liquid to enter the neutralizing pipeline mixer through the raw material switching valve, and pumping the sulfuric acid by the neutralizing concentrated sulfuric acid pump so that it enters the neutralizing pipeline mixer after passing through the neutralizing sulfuric acid flow controller to be mixed with the hemicellulose alkaline liquid for neutralization reaction in the neutralizing pipeline mixer, wherein the neutralizing concentrated sulfuric acid pump is interlocked with the neutralizing sulfuric acid controller, and the neutralizing sulfuric acid controller is interlocked with the neutralization pH controller to control an amount of the sulfuric acid pumped by the neutralizing concentrated sulfuric acid pump so that a pH value of the neutralized hemicellulose liquid raw material is stabilized at a set value of 6.5-7.0;
at step 2, in an acid-adjusting procedure, transporting the neutralized hemicellulose liquid raw material to the acid-adjusting pipeline mixer of the acid-adjusting unit through the material pump, and pumping the concentrated sulfuric acid by the acid-adjusting concentrated sulfuric acid pump so that it enters the acid-adjusting pipeline mixer after passing through the acid-adjusting sulfuric acid controller to be mixed with the hemicellulose liquid raw material in the acid-adjusting pipeline mixer, wherein the mixed hemicellulose liquid enters the acid-adjusting tank for temporary storage, and the acid-adjusting sulfuric acid controller is linked with the material flow controller to adjust a pumping amount of the acid-adjusting concentrated sulfuric acid pump according to the flow rate of the hemicellulose liquid raw material to enable an acidity of the hemicellulose liquid raw material to satisfy a set requirement of 1%-4%;

at step 3, in a feeding procedure, transferring to the feed tank of the feeding unit the acid-adjusted hemicellulose liquid overflowing from the acid-adjusting tank; wherein when a liquid level of the feed tank reaches 25%-35%, the feed valve switch is turned on and the feed pump is started so that the hemicellulose liquid enters a subsequent procedure;

at step 4, in a liquefaction ejecting procedure, after flowing the hemicellulose liquid through the plate-type feed and discharge heat exchanger, transferring the hemicellulose liquid into the liquefaction ejector for mixing with an external high-pressure vapor in the liquefaction ejector and ejecting the heat-exchanged hemicellulose liquid and the high-pressure vapor into the liquefaction maintainer so that the xylose liquid is obtained after hydrolysis reaction occurs between the hemicellulose liquid and high-pressure vapor in the liquefaction maintainer; wherein the liquefaction temperature controller is linked with the temperature regulating valve, and the temperature regulating valve controls an opening degree of the liquefaction ejector to maintain a stable temperature of the liquefaction maintainer so as to facilitate hydrolysis of the hemicellulose liquid;

at step 5, in a feed and discharge heat-exchanging procedure, passing the obtained xylose liquid through the plate-type feed and discharge heat exchanger to exchange heat with the hemicellulose liquid from the feed pump to reduce the temperature of the xylose liquid, wherein the temperature of the hemicellulose liquid is increased due to residual heat of the hemicellulose liquid, and the first discharge temperature sensor is interlocked with the discharge valve and the reflux valve of the discharge controlling unit; when the first discharge temperature sensor senses that the temperature of the xylose liquid is not lower than a set value, the discharge valve of the discharge controlling unit is opened, the reflux valve of the discharge controlling unit is closed, and the xylose liquid is discharged normally;

wherein otherwise, the reflux valve is opened, the discharge valve is closed, and the xylose liquid flows back into the feed tank for recirculation; and at step 6, in a discharge controlling procedure, transferring the heat-exchanged xylose liquid into the plate-type discharge heat exchanger to exchange heat with cooling water flowing through the plate-type discharge heat exchanger, and after flowing the xylose liquid through the discharge pressure adjusting valve and the second discharge temperature controller, discharging the xylose liquid.

8. The method according to claim 7, wherein at step 4, a temperature of the liquefaction temperature controller is set from 128° C. to 130° C.

9. The method according to claim 7, wherein at step 5, a temperature of the first discharge temperature sensor is set from 115° C. to 120° C.

10. The method according to claim 7, wherein at step 6, a discharge temperature of the xylose liquid is from 60° C. to 80° C. with a pressure ranging from 0.20 MPa to 0.30 MPa.

11. The method according to claim 7, wherein the hemicellulose liquid and high pressure vapor are maintained in the liquefaction maintainer for the hydrolysis reaction for 2.0 h to 3.0 hours.

12. A system for preparing xylose liquid by continuously hydrolyzing hemicellulose, comprising a neutralizing unit, an acid-adjusting unit, a feeding unit, a liquefaction ejecting unit, a feed and discharge heat-exchanging unit and a discharge controlling unit, wherein:

the neutralizing unit comprises a hemicellulose liquid-containing raw material tank, a neutralizing concentrated sulfuric acid pump and a neutralizing pipeline mixer, the acid-adjusting unit is configured to receive mixed material from the neutralizing material and comprises an acid-adjusting concentrated sulfuric acid pump, an acid-adjusting pipeline mixer and an acid-adjusting tank, the feeding unit comprises a feed tank and is configured to receive acid-adjusted, mixed material from the acid-adjusting tank, the liquefaction ejecting unit comprises a liquefaction ejector and a liquefaction maintainer and is configured to receive acid-adjusted mixed material from the feeding unit and eject a hydrolyzed, xylose liquid, the feed and discharge heat-exchanging unit comprises a plate-type feed and discharge heat exchanger is configured to exchange heat between the acid-adjusted mixed material and the hydrolyzed liquid and comprises a first discharge temperature sensor, and the discharge controlling unit comprises a discharge valve and a reflux valve;

wherein:

the first discharge temperature sensor is configured to sense a temperature of the xylose liquid obtained by the hydrolysis; and the first discharge temperature sensor is interlocked with the discharge valve and the reflux valve to control a flow direction of the xylose liquid obtained by the hydrolysis.

13. The system according to claim 12, wherein the raw material tank is configured to store a hemicellulose, alkaline, liquid raw material.

14. The system according to claim 13, wherein the acid-adjusting pipeline mixer is configured to mix the hemicellulose liquid raw material with sulfuric acid from the acid-adjusting concentrated sulfuric acid pump to obtain an acid-adjusted hemicellulose liquid.

15. The system according to claim 14, wherein the acid-adjusting tank is configured to collect the acid-adjusted hemicellulose liquid.

16. The system according to claim 12, wherein the neutralizing pipeline mixer is configured to perform a neutralization reaction of the hemicellulose alkaline liquid with sulfuric acid from the neutralizing concentrated sulfuric acid pump to obtain a hemicellulose liquid raw material.

17. The system according to claim 12, wherein the feed tank is configured to receive hemicellulose liquid overflowing from the acid-adjusting tank.

18. The system according to claim 12, wherein the plate-type feed and discharge heat exchanger is configured to exchange heat between feed of the acid-adjusted hemicellulose liquid and the xylose liquid obtained by hydrolysis.

19. The system according to claim 12, wherein the liquefaction ejector is configured to mix the heat-exchanged hemicellulose liquid with an external high-pressure vapor and eject the heat-exchanged hemicellulose liquid and the high-pressure vapor together into the liquefaction maintainer.

20. The system according to claim 19, wherein the liquefaction maintainer is configured to perform a hydrolysis reaction for the hemicellulose liquid and high-pressure vapor to obtain the xylose liquid.

\* \* \* \* \*